(12) United States Patent
Rhee et al.

(10) Patent No.: US 6,610,524 B2
(45) Date of Patent: Aug. 26, 2003

(54) THERMOSTABLE PHOSPHOLIPASE A1 MUTANTS AND A PROCESS FOR PREPARING THE SAME

(75) Inventors: Joon-Shick Rhee, Seoul (KR); Jae-Kwang Song, Taejon (KR)

(73) Assignee: Korea Advanced Institute of Science and Technology, Taejon (KR)

( * ) Notice: Subject to any disclaimer, the term of this patent is extended or adjusted under 35 U.S.C. 154(b) by 114 days.

(21) Appl. No.: 09/818,739

(22) Filed: Mar. 27, 2001

(65) Prior Publication Data

US 2002/0086355 A1 Jul. 4, 2002

(30) Foreign Application Priority Data

Sep. 15, 2000 (KR) ................................ 10-2000-0054116

(51) Int. Cl.$^7$ ............................. C12N 9/16; C12N 1/20; C12N 15/00; C12N 5/00; C07H 21/04
(52) U.S. Cl. ............... 435/196; 435/252.3; 435/252.33; 435/320.1; 435/325; 536/232
(58) Field of Search .............................. 435/196, 252.3, 435/252.33, 320.1, 325; 536/23.2

(56) References Cited

U.S. PATENT DOCUMENTS

| | | | |
|---|---|---|---|
| 5,126,155 A | 6/1992 | Palta et al. .................. | 426/331 |
| 5,744,459 A | 4/1998 | Makriyannis et al. ........ | 514/114 |

OTHER PUBLICATIONS

R. Craig Cadwell and Gerald F. Joyce, Randomization of Genes by PCR Mutagenesis, *PCR Methods and Applications*, 2:29–33 (1992).

Ichiro Watanabe et al., Molecular Cloning and Expression of the Gene Encoding a Phosopholipase A1 from *Aspergillus oryzae*, Biosci. Biotechnol. Biochem., 63(5):820–826 (1999).

MK Kim et al., Isolation of a Phospholipase A1–producing Microorganism, *J. Indus. Microbiol.*, 16:171–174 (1996).

Jae Kwang Song et al., Cloning and Expression of the Gene Encoding Phospholipase A1 from *Serratia* sp. MK1 in *Escherichia coli*, J. Biotechnology, 72:103–114 (1999).

Jae Kwang Song and Joon Shick Rhee, Simultaneous Enhancement of Technology and Catalytic Activity of Phospholipase A1 by Evolutionary Molecular Engineering, *Applied and Environmental Microbiology*, 66:890–894 (2000).

Adonis Skandalis et al., Creating Novel Enzymes by Applied Molecular Evolution, *Chemistry and Biology*, 4:889–898 (1997).

Ciaran O. Fagain, Understanding and Increasing Protein Stability, *Biochimica et Biophysica Acta*, 1252:1–14 (1995).

*Primary Examiner*—Rebecca E. Prouty
*Assistant Examiner*—Sheridan Swope
(74) *Attorney, Agent, or Firm*—Darby & Darby (57) ABSTRACT

The present invention provides thermostable phospholipase TA3 and TA13 which are mutants of phospholipase A1 involving the hydrolysis/synthesis of phospholipids, the mutated genes encoding the same, microorganisms transformed with recombinant expression vectors comprising the mutated genes and a process for preparing phospholipase A1 mutants therefrom. The process for preparing phospholipase A1 mutant of the invention comprises the steps of: culturing E. coli strain transformed with a recombinant expression vector comprising a gene coding for phospholipase A1 mutant derived from Serratia sp.; and, isolating and purifying phospholipase A1 mutant from the culture. Since phospholipase A1 mutants of the invention have been improved in terms of thermal stability and enzyme activity as well, they can be practically applied to various biological process, pharmaceutics, cosmetics and food industries.

7 Claims, 4 Drawing Sheets

SEQUENCE LISTING

<160> NUMBER OF SEQ ID NOS: 7

<210> SEQ ID NO 1
<211> LENGTH: 963
<212> TYPE: DNA
<213> ORGANISM: Serratia sp.

<400> SEQUENCE: 1

```
atgagtatgt ctttgagttt tacctctgcg atcgcccag cagccattca gccccgatg      60 gtgcgtacgc aaccagaacc gttgagttcc tcgcagcctg tagaagcttc tgcaacaaag     120
gctccggtgg ccacgctttc ccaaaacagc ctgaacgccc agagcctgct gaacacgctg     180
gtcagcgaga tatcggcagc cgcgccggcg gcggcgaacc agggcgtgac gcgcgggcag     240
cagccacaga aggggacta tacgctggcg ttactggcta aagacgttta cagcaccggt     300 agtcaggag tcgaaggttt caaccggttg agcgccgacg ccttgctggg tgccggcatt     360
gaccctgcca gtctgcagga tgcggcatcg ggttttcagg ccgggattta cacggataat     420
cagcagtatg tgttggcctt cgccggcacc aatgatatgc gcgactggtt gagcaacgtg     480
cgccaggcga ccggctatga cgatgtgcag tacaatcagg cggtatccct tgcgaaaagc     540
gccaaggcag cctttggtga tgcgctggtg atcgccggtc attcgcttgg cggcggtctg     600
gcggctacgg cagcgctggc gacgggcacg gtggcggtga cttttaacgc tgcggggggt     660
tccgactata cgctgaatcg tatgggatc gatccggcag cggcgaagca ggatgcacaa     720 gccggggta tccgccgtta cagcgagcaa tacgacatgc tgaccggaac gcaggaatcc     780
acttcgctga tcccggatgc catcgggcat aaatcacgc tggccaataa cgacaccctg     840
agcggcattg acgactggcg cccgagcaaa cacctggatc gcagcctgac ggctcacggg     900
attgataagg tgatcagttc gatggcggag caaaagccat gggaggcgat ggccaatgcc     960
tga                                                                    963
```

<210> SEQ ID NO 2
<211> LENGTH: 31
<212> TYPE: DNA
<213> ORGANISM: Artificial Sequence
<220> FEATURE:
<223> OTHER INFORMATION: Forward primer for mutagenic PCR

<400> SEQUENCE: 2
cggaattctt tgagttttac ctctgcgatc g         31

<210> SEQ ID NO 3
<211> LENGTH: 32
<212> TYPE: DNA
<213> ORGANISM: Artificial Sequence
<220> FEATURE:
<223> OTHER INFORMATION: Reverse primer for mutagenic PCR

<400> SEQUENCE: 3
gcggatccca tcaggcattg gccatcgcct cc        32

<210> SEQ ID NO 4
<211> LENGTH: 963
<212> TYPE: DNA
<213> ORGANISM: Artificial Sequence
<220> FEATURE:
<223> OTHER INFORMATION: DNA sequence of mutant phospholipase A1, TA3

<400> SEQUENCE: 4
atgagtatgt ctttgagttt tacctctgcg atcgccccag cagccattca gccccgatg         60
gtgcgtacgc aaccagaacc gttgagttcc tcgccgcctg tagaagcttc tgcagcaaag       120
gctccggtgg ccacgctttc ccaaaacagc ctgaacgccc agagcctgct gaacacgctg       180
gtcagcgaga tattggcagc cgcgccggcg gcggcgaacc agggcgtgac gcgcgggcag       240
cagccacaga aggggactat acgctggcgt tactggcta aagacgttta cagcaccggt       300
agtcagggag tcgtaggttt caaccggttg agcgccgacg ccttgctggg tgccggcatt       360
gaccctgcca gtctgcagga tgcggcatcg gttttcagg ccgggattta cacggataat       420
cagcagtatg tgttggcctt cgccggcacc aatgatatac gcgactggtt aatcaacgtg       480
cgccaggcga ccggctatga cgatgtgcag tacaatcagg cggtatccct tgcgaaaagc       540
gccaaggcag cctttggtga tgcgctggtg atcgccggtc attcgcttgg cggcggtctg       600
gcggctacgg cagcgctggc gacgggcacg gtggcggtga cttttaacgc tgcggggtt       660
tccgactata cgctgaatcg tatgggatc gatccggcag cggcgaagca ggatgcacaa       720
gccgggggta tccgccgtta cagcgagcaa tacgacatgc tgaccggaac gcaggaatcc       780
acttcgctga tcccggatgc catcgggcat aaaatcacgc tggccaataa cgacacactg       840
agcggcattg acgactggcg cccgagcaaa cacctggatc gcagcctgac ggctcacggg       900
attgataagg tgatcagttc gatggcggag caagagccat gggaggcgat ggccaatgcc       960
tga                                                                      963

<210> SEQ ID NO 5
<211> LENGTH: 963
<212> TYPE: DNA
<213> ORGANISM: Artificial Sequence
<220> FEATURE:
<223> OTHER INFORMATION: DNA sequence of mutant phospholipase A1, TA13

<400> SEQUENCE: 5

```
atgagtatgt ctttgagttt tacctctgcg atcgccccag cagccattca gcccccgatg    60
gtgcgtacgc aaccagaacc gttgagttcc tcgcagcctg tacaagcttc tgcaacaaag   120
gctccggtgg ccacgctttc ccaaaacagc ctgaacgccc agagcctgct gaacacgctg   180
gtcagcgaga tatcggcagc cgcgccggcg gcggcgaacc aaggcgtgac gcgcgggcag   240
cagccacaga aggggactat acgctggcg ttactggcta agacgtttta cagcaccggt   300
```

-continued

```
                 180                 185                 190
Gly His Ser Leu Gly Gly Gly Leu Ala Ala Thr Ala Ala Leu Ala Thr
             195                 200                 205
Gly Thr Val Ala Val Thr Phe Asn Ala Ala Gly Val Ser Asp Tyr Thr
             210                 215                 220
Leu Asn Arg Met Gly Ile Asp Pro Ala Ala Lys Gln Asp Ala Gln
225                 230                 235                 240
Ala Gly Gly Ile Arg Arg Tyr Ser Glu Gln Tyr Asp Met Leu Thr Gly
                 245                 250                 255
Thr Gln Glu Ser Thr Ser Leu Ile Pro Asp Ala Ile Gly His Lys Ile
             260                 265                 270
Thr Leu Ala Asn Asn Asp Thr Leu Ser Gly Ile Asp Asp Trp Arg Pro
             275                 280                 285
Ser Lys His Leu Asp Arg Ser Leu Thr Ala His Gly Ile Asp Glu Val
             290                 295                 300
Ile Ser Ser Met Ala Glu Gln Lys Pro Trp Glu Ala Met Ala Asn Ala
305                 310                 315                 320
```

<210> SEQ ID NO 7
<211> LENGTH: 320
<212> TYPE: PRT
<213> ORGANISM: Artificial Sequence
<220> FEATURE:
<223> OTHER INFORMATION: Amino acid sequence derived from DNA sequence of
      mutant
      phospholipase A1, TA13

<400> SEQUENCE: 7

```
Met Ser Met Ser Leu Ser Phe Thr Ser Ala Ile Ala Pro Ala Ala Ile
 1               5                  10                  15
Gln Pro Pro Met Val Arg Thr Gln Pro Glu Pro Leu Ser Ser Ser Gln
             20                  25                  30
Pro Val Gln Ala Ser Ala Thr Lys Ala Pro Val Ala Thr Leu Ser Gln
         35                  40                  45
Asn Ser Leu Asn Ala Gln Ser Leu Leu Asn Thr Leu Val Ser Glu Ile
     50                  55                  60
Ser Ala Ala Ala Pro Ala Ala Ala Asn Gln Gly Val Thr Arg Gly Gln
 65                  70                  75                  80
Gln Pro Gln Lys Gly Asp Tyr Thr Leu Ala Leu Leu Ala Lys Asp Val
                 85                  90                  95
Tyr Ser Thr Gly Asn Gln Gly Val Glu Gly Phe Asn Arg Leu Ser Ala
             100                 105                 110
Asp Ala Leu Leu Gly Ala Gly Ile Asp Pro Ala Ser Leu Gln Asp Ala
         115                 120                 125
Ala Ser Gly Phe Gln Ala Gly Ile Tyr Thr Asp Asn Gln Gln Tyr Val
     130                 135                 140
Leu Ala Phe Ala Gly Thr Asn Asp Lys Arg Asp Trp Trp Ser Asn Val
145                 150                 155                 160
Arg Gln Ala Thr Gly Tyr Asp Asp Val Gln Tyr Asn Gln Ala Val Ser
                 165                 170                 175
Leu Ala Lys Ser Ala Lys Ala Ala Phe Gly Asp Ala Leu Val Ile Ala
             180                 185                 190
Gly His Ser Leu Gly Gly Gly Leu Ala Ala Thr Ala Ala Leu Ala Thr
         195                 200                 205
Gly Thr Val Ala Val Thr Phe Asn Ala Ala Gly Val Ser Asp Tyr Thr
     210                 215                 220
```

-continued

```
            210                 215                 220
Leu Asn Arg Met Gly Ile Asp Pro Ala Ala Ala Lys Gln Asp Ala Gln
225                 230                 235                 240

Ala Gly Gly Ile Arg Arg Tyr Ser Glu Gln Tyr Asp Met Leu Thr Gly
                245                 250                 255

Thr Gln Glu Ser Thr Ser Leu Ile Pro Asp Ala Ile Gly His Lys Ile
            260                 265                 270

Thr Leu Ala Asn Asn Asp Thr Gln Ser Gly Ile Asp Asp Trp Arg Pro
        275                 280                 285

Ser Asn His Leu Asp Arg Ser Leu Thr Ala His Gly Ile Asp Lys Val
    290                 295                 300

Ile Ser Ser Met Ala Glu Gln Lys Pro Trp Glu Ala Met Ala Asn Ala
305                 310                 315                 320
```

THERMOSTABLE PHOSPHOLIPASE A1 MUTANTS AND A PROCESS FOR PREPARING THE SAME

BACKGROUND OF THE INVENTION

1. Field of the Invention

The present invention relates to phospholipase A1 mutants and a process for preparing the same, more specifically, to thermostable phospholipase TA3 and TA13 which are mutants of phospholipase A1 catalyzing the reaction of hydrolysis/synthesis of phospholipids, genes encoding the same, microorganisms transformed with recombinant expression vectors comprising the mutant genes and a process for preparing phospholipase A1 mutants therefrom.

2. Background of the Invention

It has been known that: lysophospholipid not only plays a role in platelet aggregation, but also mediates physiological activity such as signal transduction in animal (see: Durieux and Lynch, Trends Pharmacol. Sci., 14: 249, 1993), and also functions as a plant hormone to prevent plants or fruits from over-ripening (see: U.S. Pat. No. 5,126,155). Since lysophospholipid is highly soluble in water and forms stable emulsion under various hydrogen ion concentrations and broad range of temperature and has stability in the presence of magnesium or calcium ion, it has been applied to many industrial uses as an emulsifier such as pharmaceutics, cosmetics and food processing.

In biochemical pathway, lysophospholipid is formed via hydrolysis of phospholipid by phospholipase A1: that is, phospholipase A1 hydrolyzes 1-fatty acyl group (or fatty acyl group in the sn-1 position) of phospholipid to form lysophospholipid and fatty acid. The phospholipase A1 is an essential enzyme in the synthesis of phospholipids such as polyunsaturated fatty acids(PUFA) such as DHA or EPA. In physiological aspects, phospholipase A1 is related to human phospholipidosis caused by accumulation of phospholipid in lysosome due to the inhibition of phospholipase activity by cationic amphiphilic drug(CAD) (see: Reasor et al., Proc. Soc. Biol. Med., 212:297–304, 1996). Although phospholipase A1 has been isolated from a variety of sources such as mammals, snake toxins, bee toxins and microorganisms including Serratia sp. and Aspergillus sp., low stability of the enzymes hampered their application to biological processes.

The stability of enzyme is one of the most crucial factors in biological process where the enzyme is employed as a biological catalyst. Especially, the efficiency of biological catalysis performed at high temperature is shown to be relatively higher than that performed at low temperature. Hence, the thermostability of enzyme is the major concern in the biological process. In addition, enzyme reaction at high temperature has several advantages over enzyme reaction at room temperature or low temperature like high substrate solubility, reduced microbial contamination, lower viscosity of the reaction mixture, etc. Therefore, development of thermostable enzyme is necessary for conducting efficient biological process and for applying it for other related industry. Moreover, improved thermal stability of the thermostable enzymes is known to confer better structural stability at room temperature and confer higher resistance to denaturing factors such as organic solvents, extreme hydrogen ion concentrations and protein denaturants.

In view of the foregoings, in the preparation of phospholypase A1 for producing lysophospholipid, it is very important to prepare enzymes with improved thermal stability to enhance their enzyme activity. However, the methods proposed for synthesis of mutants of advantageous enzyme proteins, e.g., modification of protein tertiary structure by introducing disulfide bond, cross-link, salt bridge or metal binding site, are inappropriate for construction of mutants of highly active phospholipase A1 described above. Since the said modification methods can be applied only after the tertiary structure of enzyme is identified, it is impossible to apply the above methods to phospholipase A1 whose tertiary structure is not clearly understood.

Under these circumstances, it is urgently required to improve thermostability of phospholipase A1 for its universal use in biological processes. Therefore, there are strong reasons for exploring and developing novel phospholipase A1 mutants which have improved thermostability and enhanced catalytic activity as well.

SUMMARY OF THE INVENTION

The present inventors have made an effort to prepare phospholipase A1 mutants with improved thermostability which can be applied to various biological processes, and prepared phospholipase A1 mutants with substantially improved thermostability compared with the naturally occurring enzyme by introducing random mutations into the phospholipase A1 gene using a recombinant vector containing naturally occurring phospholipase A1 gene derived from Serratia sp. as a template for mutagenic polymerase chain reaction (PCR), followed by transforming the recombinant expression vector into E. coli.

The first object of the invention is, therefore, to provide phospholipase A1 mutants derived from Serratia sp. strain MK1.

The second object of the invention is to provide genes encoding the mutants.

The third object of the invention is to provide recombinant expression vectors comprising the mutated genes.

The fourth object of the invention is to provide E. coli strains transformed with the recombinant expression vectors.

The fifth object of the invention is to provide a process for preparing phospholipase A1 mutants.

BRIEF DESCRIPTIONS OF DRAWINGS

The above and the other objects and features of the present invention will become apparent from the following descriptions given in conjunction with the accompanying drawing, in which.

DETAILED DESCRIPTION OF THE INVENTION

The process for preparing phospholipase A1 mutants of the invention comprises the steps of: culturing E. coli strains transformed with recombinant expression vectors comprising phospholipase A1 mutant genes; and, isolating and purifying phospholipase A1 mutants therefrom.

The recombinant expression vectors comprising phospholipase A1 mutant genes were attained as follows: A recombinant vector comprising 963 bp DNA of naturally occurring phospholipase A1 gene(SEQ ID NO: 1) derived from Serratia sp. was first constructed, and random mutations were introduced into the said naturally occurring phospholipase A1 DNA by mutagenic polymerase chain reaction (PCR) using the recombinant vector as a template, and then, the mutated DNA was inserted into an appropriate expression vector. The recombinant expression vectors thus obtained were transformed into E. coli to prepare a library of phospholipase A1 mutants. The library of E. coli transformed with recombinant expression vectors comprising phospholipase A1 mutant DNA was heated at 70° C. to 90° C. and screened for thermostable phospholipase A1 expression by filter-based visual screening method.

The nucleotide sequences of the thermostable phospholipase A1 mutant DNAs were determined by the conventional method, and thermostable phospholipase A1 mutants having 6 and 7 amino acid substitutions compared with the amino acid sequence of naturally occurring phospholipase A1 were identified. In this regard, the mutants were named 'phospholipase TA3' and 'phospholipase TA13', respectively. Phospholipase TA3 was identified to have amino acid substitutions at positions of 32, 39, 65, 105, 153, 158 and 303 with P, A, L, V, I, I, and E, and phospholipase TA13 was identified to have substitutions at positions of 36, 102, 154, 158, 281 and 291 with Q, N, K, W, Q and N, respectively.

Figure 1:
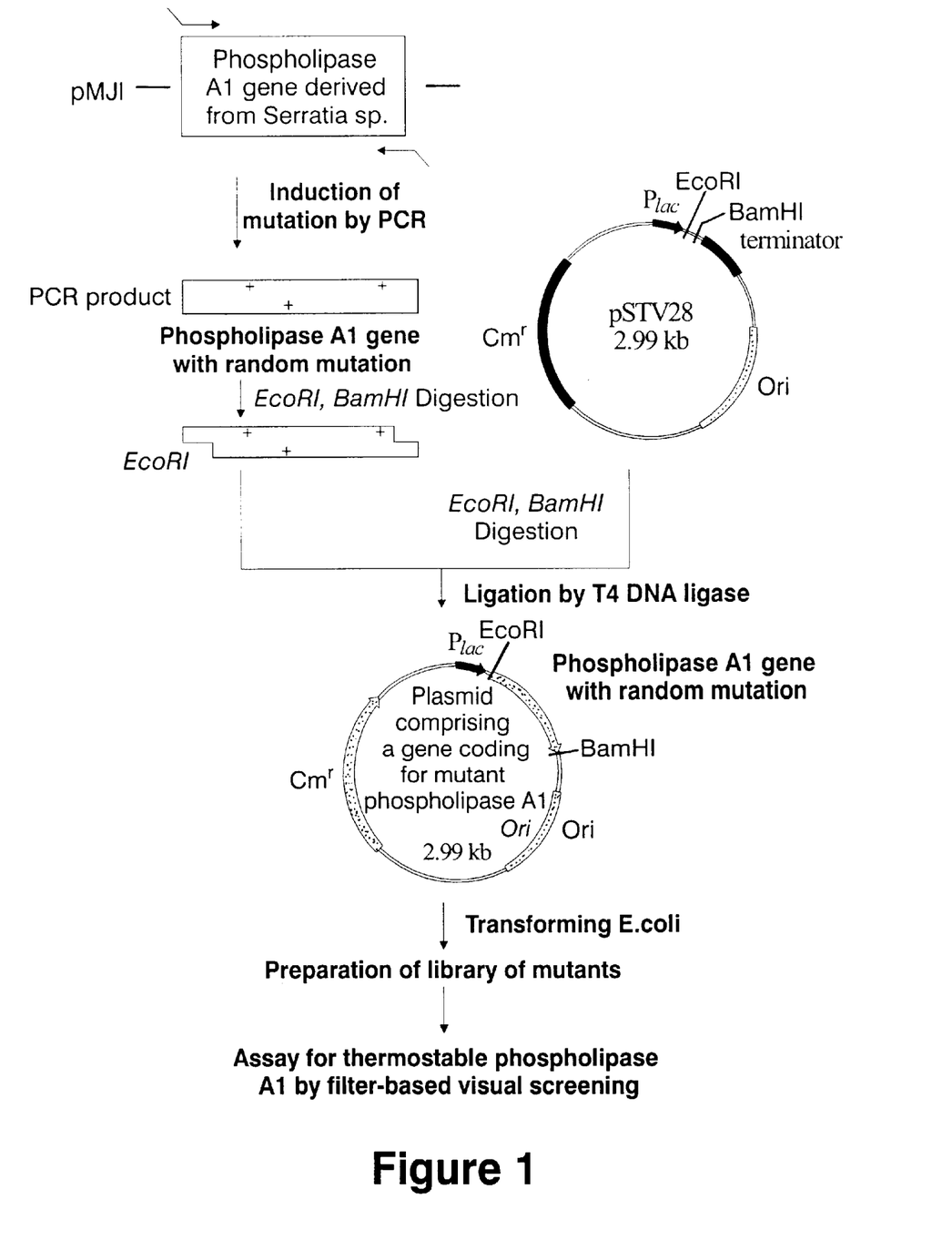
FIG. 1 is a schematic representation of a process for preparing thermostable phospholipase A1 mutants of the invention.

In the preferred examples of the present invention, recombinant expression vectors containing phospholipase A1 mutant genes, pTA3 and pTA13, were constructed and transformed into E. coli XL-Blue to obtain tranformants, which were named "Escherichia coli XL-Blue/pTA3" and "Escherichia coli XL-Blue/pTA13", respectively. These transformants were deposited at Korea Research Institute of Bioscience and Biotechnology (KRIBB) located at #52, Oun-dong, Yusong-ku, Taejon 305–333, Republic of Korea on Aug. 10, 2000 as deposit no. KCTC-18037P for *Escherichia coli* XL-Blue/TA3 and deposit no. KCTC-18038P for *Escherichia coli* XL-Blue/TA13, and converted under the terms of Budapest Treaty on Sep. 25, 2000 as accession nos. KCTC0866BP and KCTC0867BP, respectively. A preferred example preparing thermostable phospholipase A1 mutants of the invention is schematically depicted in FIG. 1.

Since the improvement of stability at high temperature may cause reduction of catalytic activity, the activity of thermostable phospholipase mutants, TA3 and TA13, was investigated for phospholipid hydrolysis at high temperature. The result showed elevated optimum temperature and enhanced catalytic activity thereat relative to the naturally occurring enzyme. Since phospholipase A1 mutants of the invention have been improved in terms of thermal stability and enzyme activity as well, they can be practically applied to various biological process, pharmaceutics, cosmetics and food industries.

The present invention is further illustrated in the following examples, which should not be taken to limit the scope of the invention.

EXAMPLE 1

Construction of Phospholipase A1 Mutant Library

The various mutants of phospholipase A1 were prepared by introducing random mutations into phospholipase A1 gene by employing mutagenic polymerase chain reaction (PCR) technique: first, a recombinant plasmid pMJ1 was constructed by insertion of 963 bp of naturally occurring phospholipase A1 DNA(SEQ ID NO: 1) derived from Serratia sp. strain MK1 (see: Song, J. K. et al., J. Biotechnol., 72: 103–114, 1999) into pUC19, which was then used as a template for mutagenic PCR. The primers for mutagenic PCR, i.e., N-terminal primer and C-terminal primer shown below, were synthesized based on the nucleotide sequence of naturally occurring phospholipase A1 gene derived from Serratia sp. strain MK1.

```
N-primer (SEQ ID NO:2):
    5'-CGGAATTCTTTGAGTTTTACCTCTGCGATCG-3'

C-primer (SEQ ID NO;3):
    5'-GCGGATCCCATCAGGCATTGGCCATCGCCTCC-3'
```

PCR reaction mixture containing 0.1 $\mu$M of each said primer, 5 ng of recombinant plasmid pMJ1 as a template, 10 mM Tris-HCl (pH 8.3), 50 mM KCl, 7 mM $MgCl_2$, 0.1 mM $MnCl_2$, 0.2 mM dGTP, 1 mM dCTP, 1 mM dTTP and 5 unit of Taq polymerase in a total volume of 100 $\mu$l was prepared. Then, the reaction mixture was subjected to repeating following steps: 1 minute (10 minutes for the first cycle) at 94° C., 1 minute at 60° C., and 1 minute (10 minutes for the last cycle) at 72° C. for 25 cycles. Then, secondary mutagenic PCRs were performed with thermostable mutant genes isolated above as templates, under the same condition as above.

To construct recombinant plasmids, amplified PCR product was isolated by agarose gel electrophoresis, followed by cutting with the restriction enzymes EcoRI and BamHI, and then ligation to an expression vector pSTV28 (Takara Shuzo, Japan) which has been known to be highly efficient for the expression of mutant phospholipase A1 (PLA). The recombinant expression vectors comprising the above constructed mutant genes were transformed into E. coli XL1-Blue (recA1 endA1 gyrA96 thi-1 hsdR17 supE44 relA1 [F' proAB lacI$^q$ Z$\Delta$15 Tn10 (Tet$^r$)], Stratagene, U.S.A.) to prepare phospholipase A1 mutant library.

EXAMPLE 2

Screening of Phospholipase A1 Mutants

Phospholipase A1 mutant library prepared in Example 1 was spreaded onto LB agar plate containing 0.5% bactotrypton, 1% yeast extract, 1% NaCl and 1.5% agar. To screen phospholipase A1 mutants by filter-based visual screening, the library was transferred to nylon membrane, and then placed on LB plate for E. coli host cells to grow and form library on the nylon membrane. And then, cells grown on the membrane were subjected to three step lysis by placing the membrane on the paper filter dipped in following solutions in order. The conditions of each lysis step are as follows:

(i) 25 mM Tris-HCl (pH 8.0), 1 mg/ml lysozyme, 1 mM EDTA (pH 8.0), 15 minutes;

(ii) 10 mM Tris-HCl (pH 8.0), 0.1% Triton X-100, 30 minutes; and, (iii) 50 mM Tris-HCl (pH 8.0), 30 minutes In order to screen mutants of phospholipase A1 for their thermostablity, the membrane processed through the above steps was subjected to the first heat treatment by incubating at temperature above 70° C. for 2 hours and to the second heat treatment at 80° C. for 3 hours, consecutively.

Then, to screen mutants for their catalytic activity, the heat-treated library on the membrane was incubated in a PCY plate comprising 1% agarose, 0.8% phosphatidylcholine, 20 mM $CaCl_2$, 0.4% taurocholic acid and 50 mM Tris-HCl (pH 8.0) at 42° C. for 2 hours. Subsequently, mutants forming clear haloes on the plate as a result of sustaining catalytic activity were selected from wild-type phospholipase A1 which did not form halo. Through the screening procedure, two clones containing thermostable phospholipase A1 gene which have enhanced thermal stability, as well as improved catalytic activity at high temperature were isolated.

Preparation of thermostable phospholipase A1 mutants described in Examples 1 and 2 are schematically depicted in FIG. 1.

EXAMPLE 3

Determination of Nucleotide Sequences of Phospholipase A1 Mutants

Figure 2A:
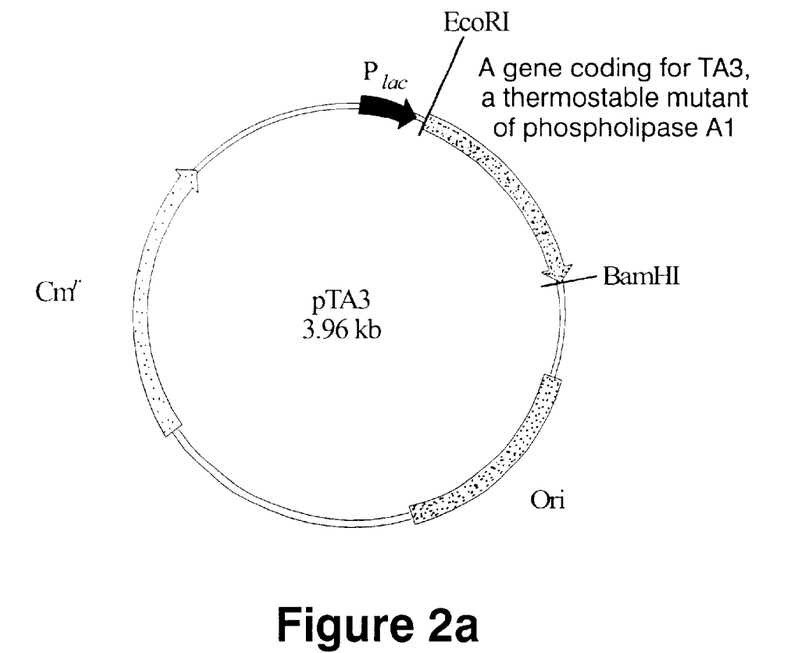
FIG. 2a is a genetic map of recombinant expression vector, pTA3 which comprises phospholipase A1 mutant gene, TA3.
Figure 2B:
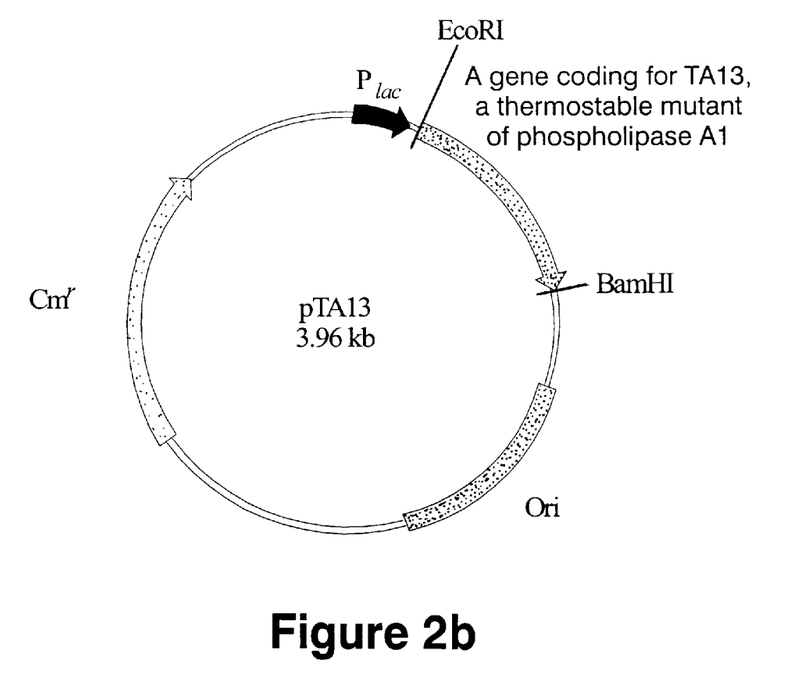
FIG. 2b is a genetic map of recombinant expression vector, pTA13 comprises phospholipase A1 mutant gene, TA13.

The nucleotide sequences of phospholipase A1 mutants were determined by using ABI PRISM BioDye Primer cycle sequencing kit and AmpliTaq DNA polymerase (Perkin-Elmer, U.S.A.), and set forth in SEQ ID NO: 4 (phospholipase TA3) and SEQ ID NO: 5 (phospholipase TA13), respectively, then the name, TA3, was given to phospholipase A1 mutant with SEQ ID NO: 4 and the name, TA13, was given to phospholipase A1 mutant with SEQ ID NO: 5. Also, genetic maps for plasmids comprising TA3 and TA13 are provided in FIG. 2a and 2b, respectively.

The amino acid sequence of TA3 was deduced from the nucleotide sequence of TA3 comprising thermostable phospholipase A1 mutant gene and set forth in SEQ ID NO: 6, and the amino acid sequence of TA13 was deduced from the nucleotide sequence of TA13 and set forth in SEQ ID NO: 7. When the amino acid sequences of thermostable phopholipase mutants, TA3 and TA13 were compared with that of naturally occurring phospholipase A1, TA3 and TA13 were identified as novel proteins with 7 and 6 amino acid substitutions, respectively. Phospholipase TA3 has been identified to have amino acid substitutions at positions of 32, 39, 65, 105, 153, 158 and 303 with P, A, L, V, I, I, and E and phospholipase TA13 has been identified to have amino acid substitutions at positions of 36, 102, 154, 158, 281 and 291 with Q, N, K, W, Q and N, respectively.

Based on amino acid sequences and catalytic activity shown by filter-based visual screening described above, TA3 and TA13 of the present invention were found to be novel phospholipase A1's which have different amino acid sequences from that of naturally occurring phospholipase A1, as well as have improved stability at high temperature.

EXAMPLE 4

Production of Phospholipase A1 Mutants

*Escherichia coli* XL1-Blue was transformed with pTA3 and pTA13 which are designed to have Histidine-tag on thermostable phospolipase A1 and constructed to express thermostable enzymes continuously. Histidine-tag, introduced for easy purification of thermostable enzymes, enables single step purification by employing nickel-nitrotriacetic agarose resin. Each recombinant *E. coli* XL1-Blue/pTA3 and XL-Blue/pTA13, was inoculated into 100 ml aliquot of a TYSPN liquid culture medium containing 2% bacto-trypton, 1% yeast extract, 0.5% $Na_2HPO_4$, 1% $KNO_3$ and 0.5% NaCl, followed by incubation at 30° C. under a rotary shaking condition of 200 rpm. Until the cell concentration reached to $OD_{600}$ of about 3.0, cells were incubated to express thermostable phospolipase A1 mutant continuously, and then harvested by centrifugation at a speed of 7000 rpm for 10 minutes.

The recombinant *E. coli* cells thus obtained were suspended in cell lysis buffer (50 mM phosphate buffer(pH 8.0) containing 300 mM NaCl, 10 mM imidazole, 0.05% Triton X-100, 10% glycerol), followed by sonication to disrupt cells. After centrifugation of cell lysate to obtain a supernatant, the supernatant was adsorbed into nickel-nitrotriacetic acid agarose resin, which was then washed with washing buffer several times, followed by elution of thermostable phospholipase A1 mutant with 250 mM imidazole solution. The eluted enzyme solution was passed through Sephacryl S-200 resin to obtain pure thermostable phospholipase A1 mutant. SDS-PAGE analysis of purified enzyme revealed over 99% purity of thermostable phospholipase A1 mutant, which was found to be water soluble and to sustain phospholipase activity.

Since thermostable phospholipase A1 mutants, TA3 and TA13, were found to be efficiently prepared from *E. coli* transformed with recombinant expression vectors, pTA3 and pTA13, comprising phospholipase A1 mutant genes, these transformants were deposited at Korea Research Institute of Bioscience and Biotechnology (KRIBB) located at #52, Oun-dong, Yusong-ku, Taejon 305–333, Republic of Korea on Aug. 10, 2000 as deposit no. KCTC-18037P for *Escherichia coli* XL-Blue/TA3 and deposit no. KCTC-18038P for *Escherichia coli* XL-Blue/TA13, and converted under the terms of Budapest Treaty on Sep. 25, 2000 as accession nos. KCTC0866BP and KCTC0867BP, respectively.

EXAMPLE 5

Evaluation of Thermal Stability and Catalytic Activity of Phospholipase A1 Mutants Catalytic activity of phospholipase A1 was determined using pH-stat titration method. The amount of released fatty acid from enzyme reaction was measured at 37° C. in a pH-stat (Radiometer Copenhagen, France) equipped with autotiter and autoburette. To a substrate solution containing 3.4 mM phosphatidylcholine, 10 mM $CaCl_2$ and 2.6 mM deoxycholic acid, sonicated for emulsification, was added phospholipase A1 enzyme solution and then the amount of released fatty acid was measured. One unit is defined as the amount of enzyme that releases $1\mu$ mole of free fatty acid per minute from phosphatidylcholine at 37° C. and pH 8.0 in a pH-stat.

The thermal stability at high temperature was determined by using the enzyme purified in Example 4. The purified enzyme diluted in 50 mM phosphate buffer (pH 8.0) was aliquoted and each aliquot was incubated for 20 minutes under the condition of stepwise elevation of temperature from 50° C. to 95° C. with 5° C. increment.

Figure 3:
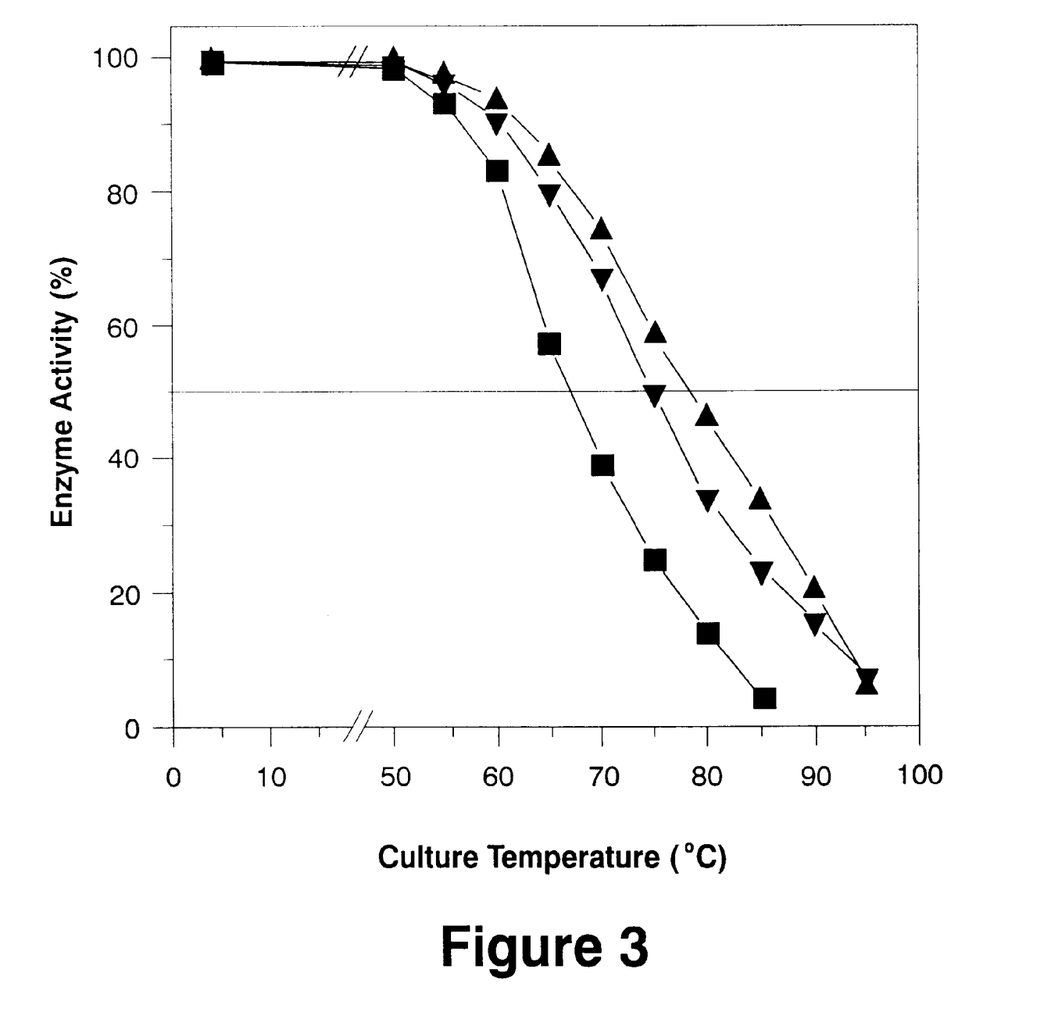
FIG. 3 is a graph showing thermal stability of thermostable phospholipase A1 mutants, TA3 (▼) and TA13 (▲) of the invention. ■ indicates thermal stability of naturally occurring phospholipase A1.

FIG. 3 is a graph showing thermal stability as enzyme activity (%) of thermostable phospholipase A1 mutants of the invention, TA3 and TA13: ■ indicates enzyme activity of naturally occurring phospholipase A1; ▼, TA3, a novel thermostable phospholipase A1 mutant; and, ▲, TA13, a novel thermostable phospholipase A1 mutant, respectively. As shown in FIG. 3, $T_m$ (the temperature at which the remaining activity is half-maximal) of TA3 increased by 7° C. and $T_m$ of TA13 increased by 11° C. Accordingly, phospholipase A1 mutants, TA3 and TA13, obtained by artificial molecular evolution were found to have much improved thermal stability relative to naturally occurring phospholipase A1.

TABLE 1

The value of enzyme kinetic parameter of various phospholipase*

| Phospholipases | $K_m$ ($\mu M$) | $K_{cat}$ ($S^{-1}$) | $K_{cat}/K_m$ ($S^{-1}$ $\mu M$) |
|---|---|---|---|
| Wild-type (PLA1) | 114.5 | 11.23 | 0.093 |
| TA3 | 105.1 | 10.92 | 0.104 |
| TA13 | 120.4 | 13.67 | 0.114 |

*The value of enzyme kinetic parameter was measured at pH 8.0 and 37° C., represented as a mean value of 2 experiments.

Figure 4:
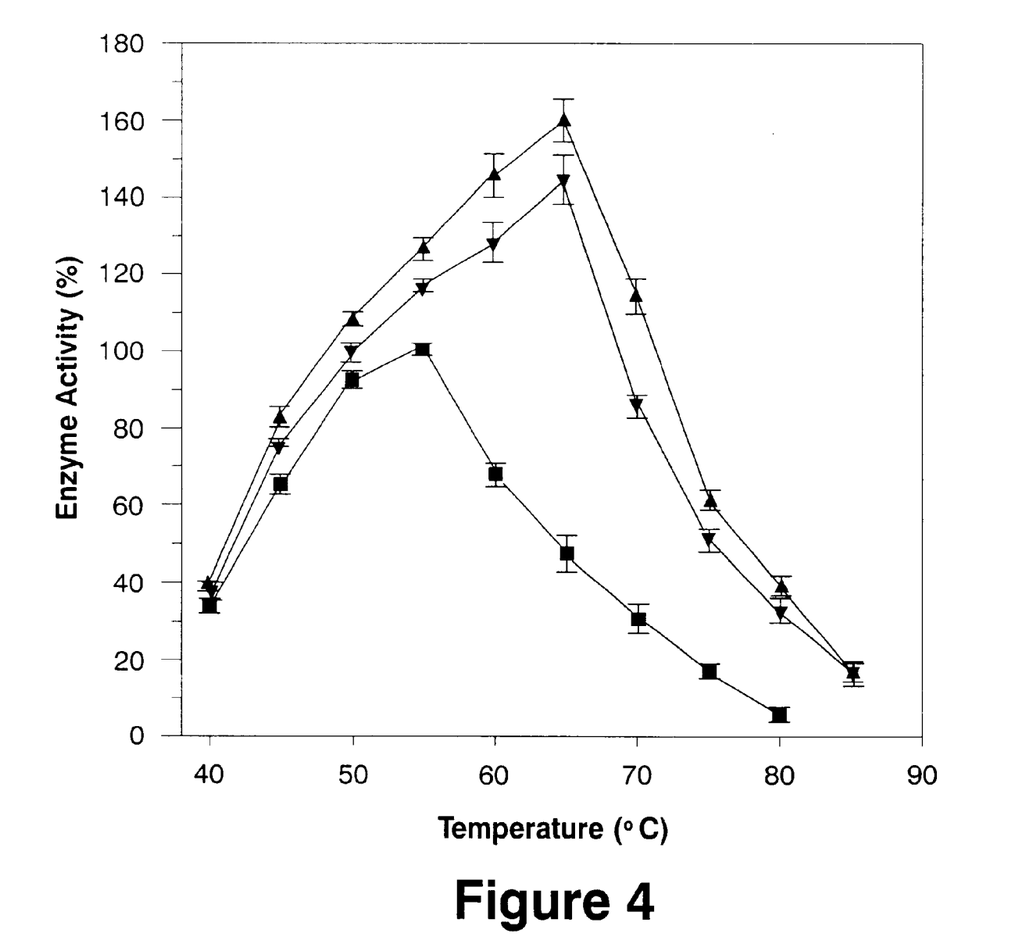
FIG. 4 is a graph showing enzyme activity of thermostable phospholipase Al mutants, TA3 (▼) and TA13 (▲) of the invention, assayed at high temperature. ■ indicates enzyme activity of naturally occurring phospholipase A1.

Since the improvement of stability at high temperature may cause reduction of catalytic activity, the activity of thermostable phospholipase mutants, TA3 and TA13, were assayed for hydrolysis of phospholipid at the indicated temperatures. FIG. 4 is a graph showing enzyme activities of thermostable phospholipase mutants, TA3 or TA13 of the invention, assayed at high temperature: ■ indicates enzyme activity of naturally occurring phospholipase A1; ▼, TA3, a novel thermostable phospholipase A1 mutant; and, ▲, TA13, a novel thermostable phospholipase A1 mutant, respectively. As shown in FIG. 4, optimum temperatures of thermostable phospholipase A1 mutants increased by 10° C., as well as enzyme activity at the optimum temperature increased by 1.6-fold relative to those of naturally occurring phospholipase A1. Accordingly, it was also confirmed that thermostable phospholipase A1 mutants of the invention have improved thermal stability, as well as enhanced enzyme activity at high temperature.

As clearly illustrated and demontrated above, the present invention provides thermostable phospholipase TA3 and TA13 which are mutants of phospholipase A1 involving the hydrolysis/synthesis of phospholipids, the mutated genes encoding the same, microorganisms transformed with recombinant expression vectors comprising the mutated genes and a process for preparing phospholipase A1 mutants therefrom. The process for preparing phospholipase A1 mutant of the invention comprises the steps of: culturing *E. coli* strain transformed with a recombinant expression vector comprising a gene coding for phospholipase A1 mutant derived from Serratia sp.; and, isolating and purifying phospholipase A1 mutant from the culture. Since phospholipase A1 mutants of the invention have been improved in terms of thermal stability and enzyme activity as well, they can be practically applied to various biological process, pharmaceutics, cosmetics and food industries.

Various modifications of the invention in addition to those shown and described herein will be apparent to those skilled in the art from the foregoing descriptions. Such modifications are also intended to fall within the scope of the appended claims.

What is claimed is:

1. A gene having the nucleotide sequence of SEQ ID NO: 4 which encodes thermostable phospholipase TA3 which is a mutant of phospholipase A1 derived from Serratia sp. strain MK1.

2. A recombinant vector comprising a gene encoding phospholipase TA3, as set forth by SEQ ID NO: 6, which is a mutant phospholipase A1 derived from Serratia sp. strain MK1.

3. An expression vector pTV3 comprising a gene encoding phospholipase TA3, as set forth by SEQ ID NO: 6, which is a mutant of phospholipase A1 derived from Serratia sp. strain MK1.

4. *Escherichia coli* XL-Blue/pTA3 (KCTC-0866BP) transformed with the expression vector pTA3 comprising a gene encoding phospholipase TA3, as set forth by SEQ ID NO: 6, which is a mutant of phospholipase A1 derived from Serratia sp. strain MK1.

5. A process for preparing a thermostable phospholipase A1 mutant comprising the steps of: culturing an *E. coli* strain transformed with a recombinant expression vector comprising a gene encoding a phospholipase A1 mutant derived from Serratia sp. wherein the phospholipase A1 mutant derived from Serratia sp. is a phospholipase TA3, as set forth by SEQ ID NO: 6, and isolating and purifying said thermostable phospholipase A1 mutant from the culture.

6. The process for preparing phospholipase A1 mutant of claim 5 wherein the expression vector comprising a gene encoding phospholipase A1 mutant derived from Serratia sp. is pTA3.

7. The process for preparing phospholipase A1 mutant of claim 5 wherein the transformed *E. coli* is *Escherichia coli* XL-Blue/pTA3 (KCTC-0866BP).

* * * * *